(12) United States Patent
Wang et al.

(10) Patent No.: US 7,274,959 B1
(45) Date of Patent: Sep. 25, 2007

(54) SYSTEM AND METHOD FOR DETECTING CARDIAC ISCHEMIA USING AN IMPLANTABLE MEDICAL DEVICE

(75) Inventors: Zifei Wang, Thousand Oaks, CA (US); Mohssen Fard, Woodland Hills, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 313 days.

(21) Appl. No.: 10/603,429

(22) Filed: Jun. 24, 2003

(51) Int. Cl.
  *A61B 5/0452* (2006.01)
(52) U.S. Cl. ..................... 600/509; 600/517
(58) Field of Classification Search ............. 600/508, 600/513, 516, 517, 509, 5, 16; 607/25, 26, 607/4, 5, 6, 9, 1, 14
See application file for complete search history.

(56) References Cited

U.S. PATENT DOCUMENTS

| | | | |
|---|---|---|---|
| 3,828,768 A | 8/1974 | Douglas | |
| 4,295,474 A * | 10/1981 | Fischell | 600/510 |
| 4,674,509 A | 6/1987 | DeCote, Jr. | |
| 4,679,144 A | 7/1987 | Cox et al. | |
| 4,799,486 A | 1/1989 | DuFault | |
| 4,974,162 A * | 11/1990 | Siegel et al. | 600/509 |
| 5,113,869 A | 5/1992 | Nappholz et al. | 128/696 |
| 5,135,004 A | 8/1992 | Adams et al. | 128/696 |
| 5,148,812 A | 9/1992 | Verrier et al. | 128/704 |
| 5,159,932 A | 11/1992 | Zanetti et al. | |
| 5,199,428 A | 4/1993 | Obel et al. | 128/419 C |
| 5,203,326 A | 4/1993 | Collins | 128/419 PG |
| 5,213,106 A * | 5/1993 | Lerner | 600/508 |
| 5,313,953 A | 5/1994 | Yomtov et al. | 128/696 |
| 5,365,426 A * | 11/1994 | Siegel et al. | 600/509 |
| 5,531,768 A | 7/1996 | Alferness | |
| 5,560,368 A * | 10/1996 | Berger | 600/517 |
| 5,560,370 A | 10/1996 | Verrier et al. | 128/705 |
| 5,643,327 A | 7/1997 | Dawson et al. | 607/24 |
| 5,792,065 A | 8/1998 | Xue et al. | |
| 5,978,710 A | 11/1999 | Prutchi et al. | |
| 6,016,443 A | 1/2000 | Ekwall et al. | 600/519 |
| 6,021,350 A | 2/2000 | Mathson | 607/17 |
| 6,081,747 A | 6/2000 | Levine et al. | 607/9 |
| 6,108,577 A | 8/2000 | Benser | 600/517 |
| 6,112,116 A | 8/2000 | Fischell et al. | 600/517 |
| 6,115,628 A | 9/2000 | Stadler et al. | 600/517 |
| 6,128,526 A | 10/2000 | Stadler et al. | 600/517 |
| 6,155,267 A | 12/2000 | Nelson | |
| 6,233,486 B1 | 5/2001 | Ekwall et al. | 607/17 |
| 6,256,538 B1 | 7/2001 | Ekwall | 607/17 |
| 6,264,606 B1 | 7/2001 | Ekwall et al. | 600/300 |

(Continued)

*Primary Examiner*—George R. Evanisko
*Assistant Examiner*—Michael Kahelin

(57) ABSTRACT

A technique is provided for detecting episodes of cardiac ischemia based on an examination of post-T-wave signal segments. Since cardiac ischemia is often a precursor to acute myocardial infarction (AMI) or ventricular fibrillation (VF), the technique thereby provides a method for predicting the possible onset of AMI or VF so that a warning may be delivered to the patient. The warning preferably includes both a perceptible electrical notification signal applied directly to subcutaneous tissue and a warning signal delivered via short range telemetry to a handheld warning device external to the patient. In one example, the onset of cardiac ischemia is identified by detecting a sharp falling edge within post-T-wave signals by filtering the signals using a high-pass filter having a cutoff frequency of at least 1 Hz. The total amount of energy in the filtered signal is calculated and compared against various thresholds.

15 Claims, 11 Drawing Sheets

U.S. PATENT DOCUMENTS

| | | |
|---|---|---|
| 6,272,379 B1 | 8/2001 | Fischell et al. ................. 607/5 |
| 6,361,503 B1 * | 3/2002 | Starobin et al. ............ 600/508 |
| 6,370,423 B1 * | 4/2002 | Guerrero et al. ............ 600/513 |
| 6,381,493 B1 | 4/2002 | Stadler et al. ................. 607/9 |
| 6,501,983 B1 | 12/2002 | Natarajan et al. ........... 600/517 |
| 6,539,259 B1 | 3/2003 | Weinberg et al. |
| 6,604,000 B2 * | 8/2003 | Lu ............................... 607/17 |
| 6,609,023 B1 * | 8/2003 | Fischell et al. ............. 600/515 |
| 6,615,075 B2 | 9/2003 | Mlynash et al. ............ 600/513 |
| 6,625,490 B1 * | 9/2003 | McClure et al. ............... 607/9 |
| 6,823,213 B1 | 11/2004 | Norris et al. |
| 2002/0151807 A1 | 10/2002 | Goldin ....................... 600/509 |
| 2003/0013974 A1 | 1/2003 | Natarajan et al. ........... 600/481 |
| 2003/0045805 A1 | 3/2003 | Sheldon et al. .............. 600/513 |
| 2003/0060724 A1 | 3/2003 | Thiagarajan et al. |
| 2003/0060854 A1 | 3/2003 | Zhu ............................ 607/25 |
| 2003/0073914 A1 * | 4/2003 | Taha et al. ................... 600/509 |
| 2003/0144700 A1 * | 7/2003 | Brown et al. ................. 607/14 |
| 2003/0153956 A1 * | 8/2003 | Park et al. .................... 607/17 |
| 2003/0208129 A1 * | 11/2003 | Beker et al. ................ 600/509 |
| 2004/0077941 A1 * | 4/2004 | Reddy et al. ................ 600/428 |
| 2004/0249420 A1 * | 12/2004 | Olson et al. ................... 607/9 |

* cited by examiner

SYSTEM AND METHOD FOR DETECTING CARDIAC ISCHEMIA USING AN IMPLANTABLE MEDICAL DEVICE

CROSS REFERENCE TO RELATED APPLICATIONS

This application is related to copending U.S. patent applications:

1) Ser. No. 10/603,398, filed Jun. 24, 2003, titled "System and Method for Detecting Cardiac Ischemia Based on T-Waves Using an Implantable Medical Device"; and 2) Ser. No. 10/606,299, filed Jun. 24, 2003, titled "System and Method for Detecting Cardiac Ischemia Based on T-Waves Using an Implantable Medical Device," which are incorporated herein by reference.

FIELD OF THE INVENTION

The invention generally relates to implantable medical devices such as pacemakers and implantable cardioverter/defibrillators (ICDs) and, in particular, to techniques for detecting cardiac ischemia.

BACKGROUND OF THE INVENTION

Cardiac ischemia is a condition whereby heart tissue does not receive adequate amounts of oxygen and is usually caused by a blockage of an artery leading to the heart tissue. If sufficiently severe, the ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death in the United States and worldwide. In other cases, although the AMI itself may not be fatal, it strikes while the victim is engaged in potentially dangerous activities, such as driving vehicles or flying airplanes, and the severe pain and possible loss of consciousness associated with AMI results in serious accidents. Even if the victim survives the AMI, quality of life may be severely restricted thereafter, because the heart is unable to adequately function due to regions of dead tissue.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less.

Accordingly, it would be highly desirable to provide a technique for reliably detecting acute myocardial ischemia so that the victim may be warned and medical attention sought. If properly warned, surgical procedures may be implemented to locate and remove the growing arterial blockage or anti-thrombolytic medications may be administered. At the very least, advanced warning would allow the victim to cease activities that might result in a fatal accident. Moreover, in many cases, AMI of VF is triggered by strenuous physical activities and so advanced warning would allow the victim to cease such activities, possibly preventing AMI or VF from occurring.

Many patients at risk of cardiac ischemia have pacemakers, ICDs or other medical devices implanted therein. Accordingly, techniques have been proposed for detecting cardiac ischemia using implanted medical devices. In particular, techniques have been developed for analyzing internal electrocardiogram (IEGM) signals in an effort to detect cardiac ischemia. See, as examples, the following U.S. Pat. Nos. 5,113,869 to Nappholz; 5,135,004 to Adams et al.; 5,199,428 to Obel et al.; 5,203,326 to Collins; 5,313,953 to Yomtov et al; 6,501,983 to Natarajan, et al.; 6,016,443, 6,233,486, 6,256,538, and 6,264,606 to Ekwall; 6,021,350 to Mathson; 6,112,116 and 6,272,379 to Fischell et al; 6,128,526, 6,115,628 and 6,381,493 to Stadler et al; and 6,108,577 to Benser. Most ischemia detection techniques seek to detect ischemia by identifying changes in the ST segment of the IEGM that are manifest during cardiac ischemia. The ST segment represents the portion of the cardiac signal between ventricular depolarization (also referred to as an R-wave) and ventricular repolarization (also referred to as a T-wave). Strictly speaking, R-waves and T-waves are features of a surface electrocardiogram (EKG). For convenience, herein, the terms R-wave and T-wave are used to refer to the corresponding internal signal component.

Problems, however, arise when attempting to detect cardiac ischemia using ST segments. Most pacemakers and ICDs initially route electrical cardiac signals through highpass filters to eliminate direct current (DC) components so that the signals can be more easily and reliably analyzed to detect relatively high frequency signal components such as P-waves, R-waves, etc. However, ST segments primarily consist of very low-frequency signals. So, to permit ST segments to be analyzed for ischemia detection purposes, the highpass filter must be configured to have a sufficiently low cutoff frequency (typically about 0.1 Hz) to allow the low frequency components of the ST segments to pass through the filter. Unfortunately, highpass filters requiring low cutoff frequencies are not well-suited for use within implantable medical devices. In particular, such filters require very large capacitors, which add significantly to the size and weight of the implantable device. Accordingly, it would be desirable to provide techniques for detecting cardiac ischemia, which do not require highpass filters with low cutoff frequencies. In addition, because the ST segment primarily consists of low-frequency signals, techniques based upon an analysis of those segments may not be particularly reliable. Accordingly, it would also be desirable to provide techniques for detecting cardiac ischemia that do not exploit the ST segment. It is to these ends that aspects of the invention are primarily directed.

Another concern with cardiac ischemia detection techniques for use in implantable medical devices is that some use fairly long range telemetry devices to transmit warning signals to external warning systems. Long range telemetry devices require a considerable amount of power and can add significantly to the size, weight and cost of the implantable device. Short range telemetry devices may not be sufficient to ensure that the warning is received. Accordingly, it would also be desirable to provide improved techniques for reliably providing warning signals that do not require long range telemetry and it is to these ends that other aspects of the invention are directed.

SUMMARY

In accordance with the invention, a technique is provided for use with an implantable medical device for detecting cardiac ischemia. Electrical cardiac signals are received and segments of the cardiac signals subsequent to ventricular repolarization are identified (i.e. post-T-wave segments). Cardiac ischemia is then detected based on an examination of the post-T-wave segments. By detecting cardiac ischemia based on post-T-wave signals, the problems noted above arising when trying to exploit ST segments are substantially overcome. In particular, as will be explained, a highpass filter having a relatively high cutoff frequency may be used, thus eliminating the need to use a low cutoff frequency filter, which typically requires a large capacitor. In an exemplary embodiment, upon detecting of the onset of an episode of cardiac ischemia, warning signals are generated, which include both a "tickle warning" applied to subcutaneous tissue and a short range telemetry warning signal transmitted to a device external to the patient. Once the tickle warning is felt, the patient positions an external warning device above the chest, which receives the short range telemetry signals and provides audible or visual verification of the ischemia warning. In this manner, the warning is reliably relayed to the patient, without requiring a long range telemetry system and so savings are achieved in power consumption, cost and other factors.

In the exemplary embodiment, the onset of cardiac ischemia is identified by detecting a sharp falling edge within post-T-wave signal segments. More specifically, cardiac signals are filtered using a high-pass filter having a cutoff frequency of at least 1 Hz. Then the total amount of energy in the filtered signal within each post-T-wave segment is calculated ($E_{PostT}$) along with a running average ($E_{PostT\_Ave}$). The sharp falling edge is then detected based upon $E_{PostT}$, $E_{PostT\_Ave}$ and first and second threshold values (Threshold$_1$ and Threshold$_2$). $E_{PostT}$ may be derived by calculating:

$$E_{PostT} = \sum_{k=Tstart}^{Tend} s(k)$$

for each post-T-wave segment, wherein s(k) is a digitized version of the filtered cardiac signal, $T_{start}$ and $T_{end}$ are start and end points, respectively, of the segment, and k represents individual samples of the digitized signal. $E_{PostT\_Ave}$ at time increment "i" may be derived by calculating:

$$E_{PostT\_Ave}(i) = \alpha \cdot E_{PostT\_Ave}(i-1) + (1-\alpha) \cdot E_{PostT}$$

where α is a "forgetting factor" set to 15/16 and wherein $E_{PostT\_Ave}(0)$ is set to a default value such as zero.

In one specific example, the onset of cardiac ischemia is detected by determining whether either $|E_{PostT} - E_{PostT\_Ave}|$ exceeds Threshold$_1$ for three consecutive heart beats or $|E_{PostT\_Ave}|$ exceeds Threshold$_2$ for three consecutive heart beats. If so, the warning signal is generated. The end of the episode of cardiac ischemia is detected by determining whether $|E_{PostT} - E_{PostT\_Ave}|$ falls below Threshold$_1$ for three consecutive heart beats while $|E_{PostT\_Ave}|$ also falls below Threshold$_2$ for the three consecutive heart beats.

Thus, improved techniques are provided for detecting cardiac ischemia and for providing reliable warning signals. Other features, objects and advantages of the invention are set forth below.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
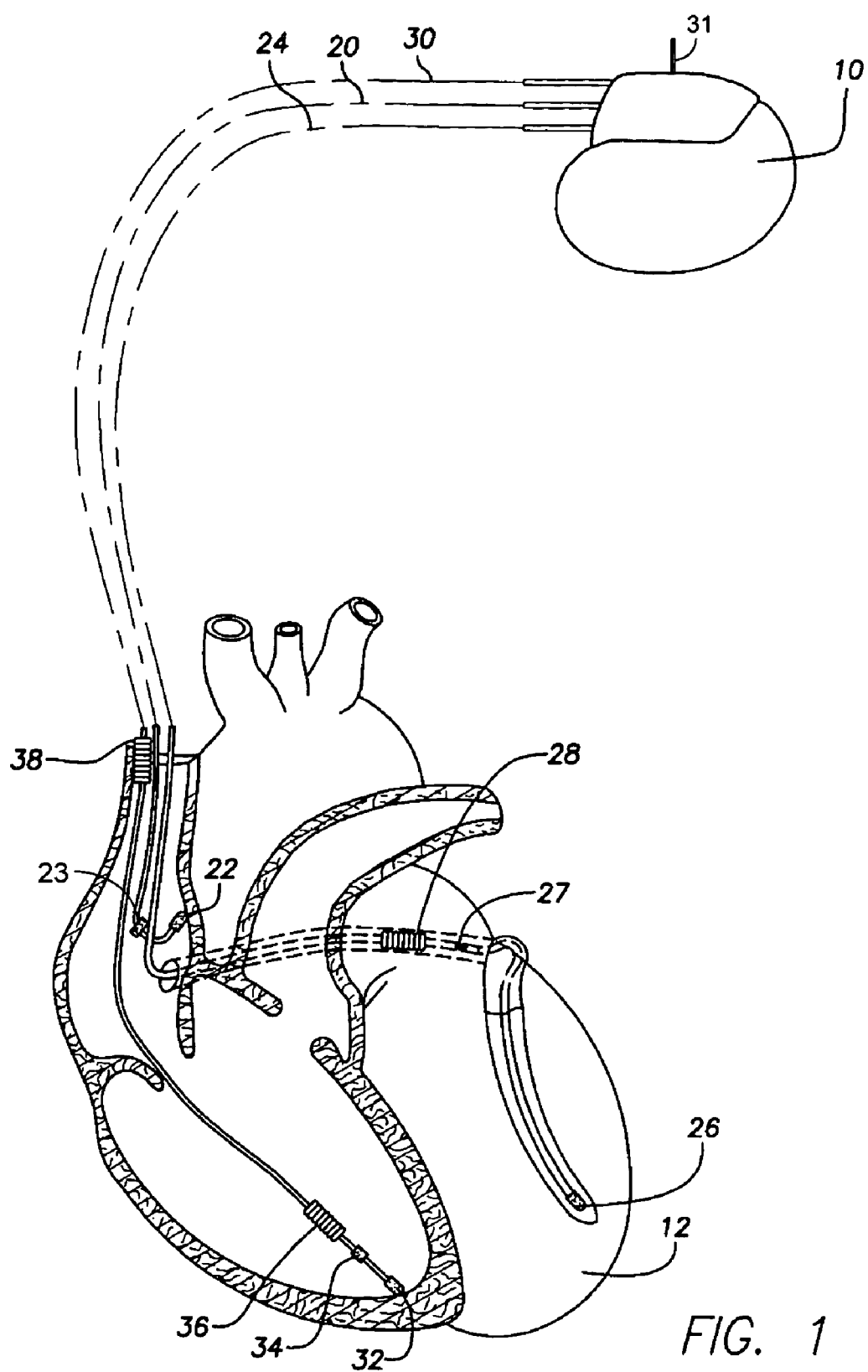
FIG. 1 is a simplified diagram illustrating an implantable stimulation device in electrical communication with at least three leads implanted into the heart of a patient for delivering multi-chamber stimulation and shock therapy including cardioversion therapy and overdrive pacing therapy.

As shown in FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "tickle warning" signal, an additional electrode 31 is provided in proximity to the device can.

Figure 2:
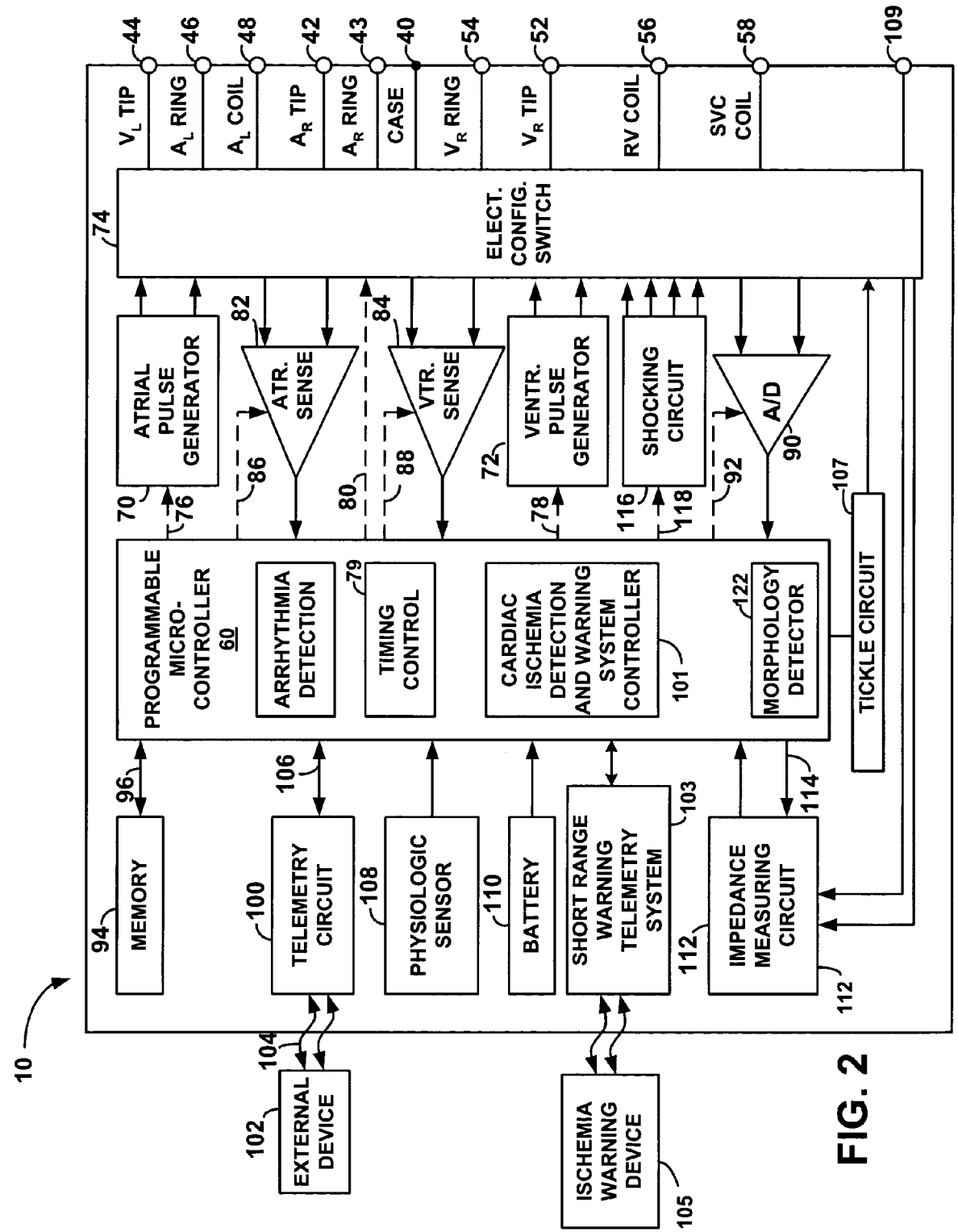
FIG. 2 is a functional block diagram of the implantable cardiac stimulation device of FIG. 1 illustrating basic elements of the stimulation device particularly including a cardiac ischemia detection and warning system for detecting cardiac ischemia based on post-T-wave signal segments.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. To provide the "tickle warning" signal, an additional terminal 109 is provided for connection to the tickle warning electrode 31 of FIG. 1.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Finally, with regard to FIG. 2, microcontroller 60 includes a cardiac ischemia detection and warning system controller 101 for controlling the detection of episodes of cardiac ischemia and for controlling the delivery of warning signals. In particular, controller 101 controls a short range telemetry system 103 to transmit warning signals to an external warning device 105. Controller 101 also controls a tickle circuit 107 that generates subcutaneous perceptible warning signals via lead 31, which is connected to electrode 109. Device case electrodes 40 may be used as the return electrode. The operation of controller 101 in combination with the other components will be described below with reference to FIG. 3 and following.

Referring to the remaining figures, flow charts, graphs and other diagrams illustrate the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Cardiac Ischemia Detection and Warning System

Figure 3:
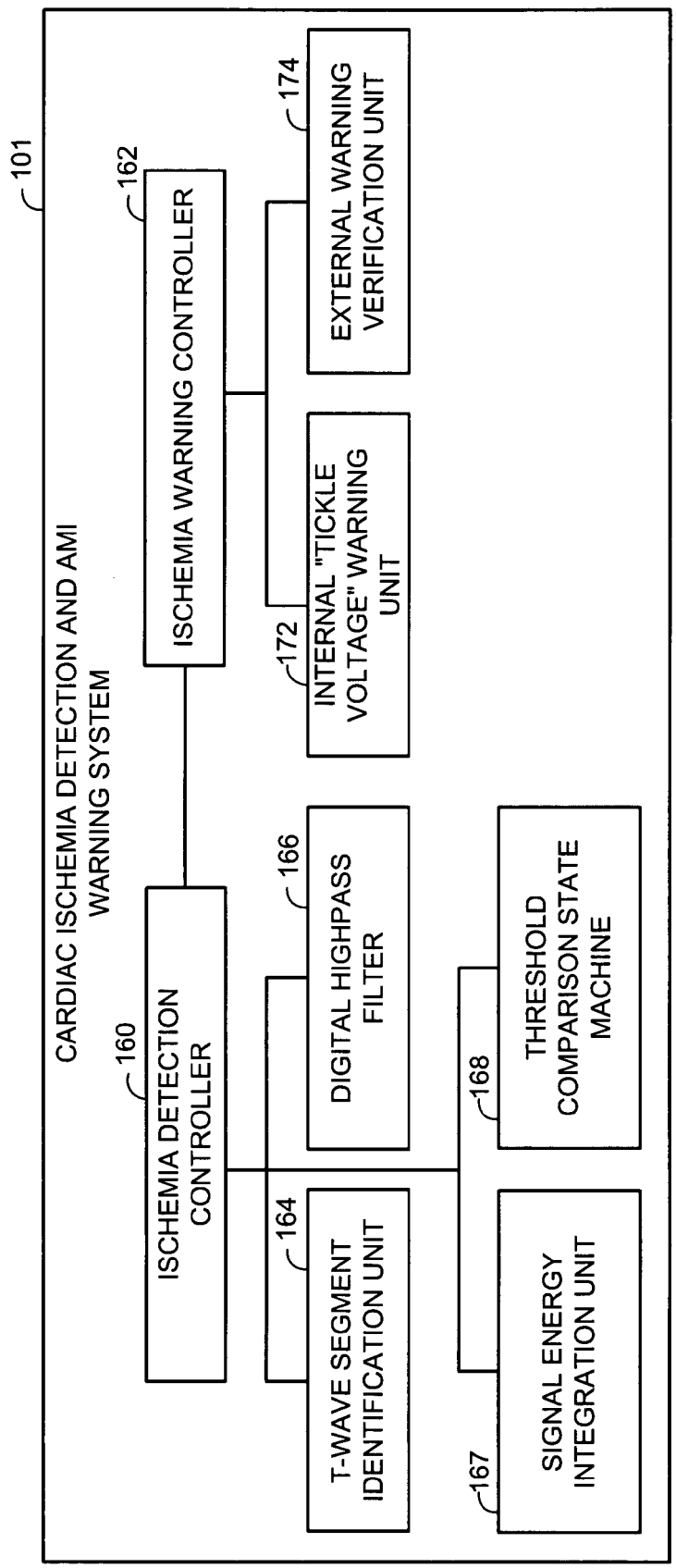
FIG. 3 is a functional block diagram of components of the cardiac ischemia detection and warning system of FIG. 2.

FIG. 3 illustrates pertinent components of cardiac ischemia detection and warning system controller 101 of FIG. 2. Briefly, the system operates to detect the onset of an episode of cardiac ischemia based on an analysis of post-T-wave segments of the IEGM and then to warn the patient by first providing an subcutaneous "tickle" voltage that the patient perceives and then by transmitting a short range verification signal to an external hand-held warning device to provide a confirmation to the patient. To this end, controller 101 includes both a cardiac ischemia detection controller 160 for coordinating units that detect the ischemia and a separate ischemia warning controller 162 for coordinating units that implement the two-step warning. T-wave segment identification unit 164 detects ventricular depolarization events (R-waves) within ventricular channel IEGM signals and identifies the location of post-T-wave segments based thereon. A digital highpass filter 166 filters the IEGM signals to exclude low frequency signals. A signal energy integration unit 167 calculates the integral of energy within post-T-wave segments of the filtered IEGM signals. A threshold comparison state machine 168 compares the energy integral along with a running average of the integral against a pair of threshold values to detect episodes of cardiac ischemia. If cardiac ischemia is detected, a tickle voltage warning unit 172 controls tickle circuit 107 (FIG. 2) to apply a perceptible subcutaneous voltage signal to the patient. An external warning verification unit controls short range warning system 103 (also FIG. 2) to send signals to hand-held ischemia warning verification device 105 (also FIG. 2) to provide verification to the patient of the ischemia warning. Alternatively, telemetry circuit 100 can be configured to transmit the verification signal to the hand-held warning device.

Figure 4:
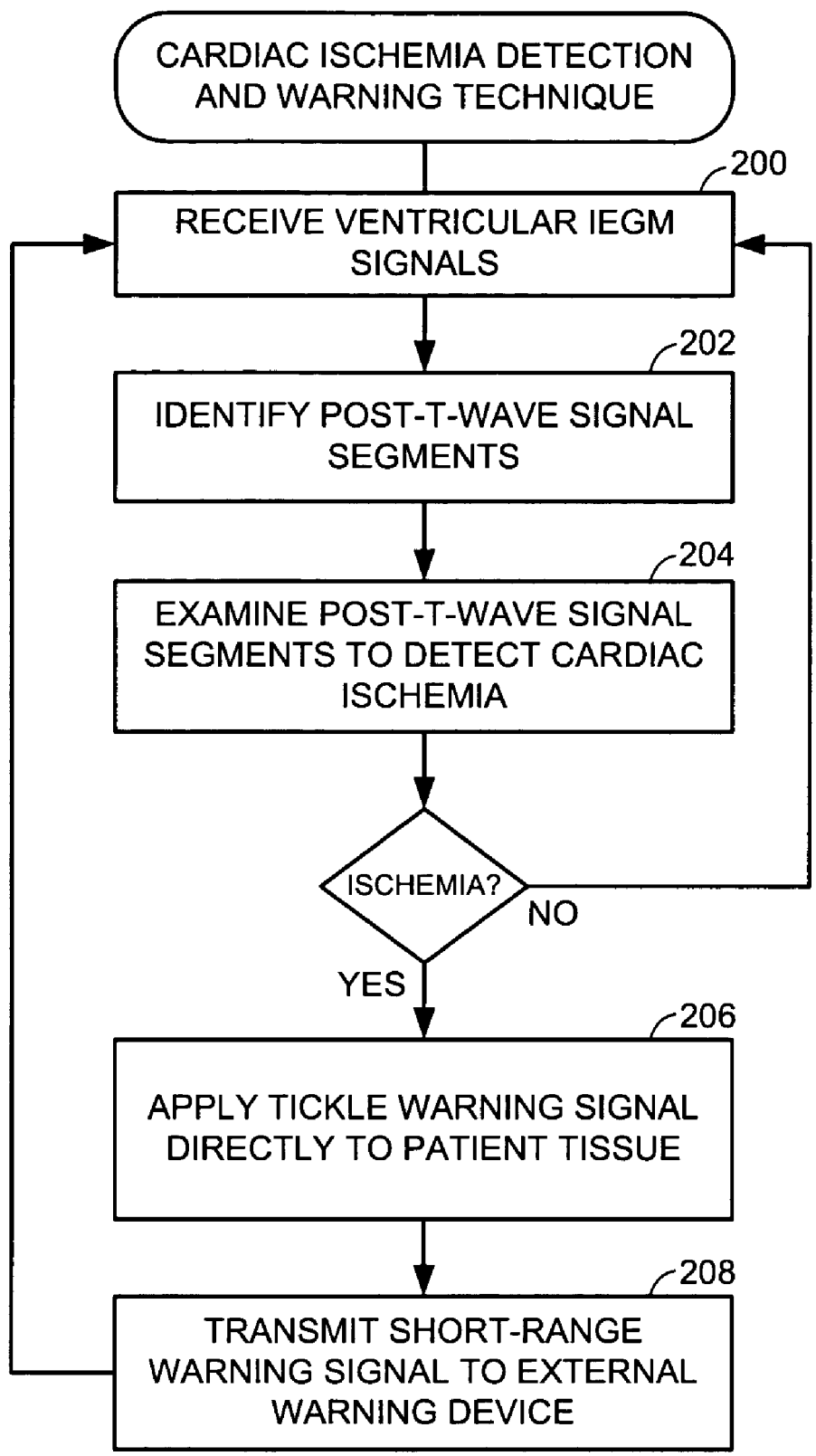
FIG. 4 is a flow chart providing an overview of an exemplary method performed by the detection and warning system of FIG. 2 for detecting cardiac ischemia and for generating warning signals.

The operation of the components of FIG. 3 will now be described in greater detail with reference to the remaining figures. Referring first to FIG. 4, ventricular IEGM signals are received at step 200. Post-T-wave signal segments are identified within the IEGM signals at step 202 using the method of FIG. 6, described below. Then the post-T-wave signal segments are examined at step 204 to detect episodes of cardiac ischemia using the technique of FIG. 7, also described below. If an episode of cardiac ischemia is detected then, at step 206, the tickle warning signal is applied to subcutaneous tissue to warn the patient of a possible subsequent AMI or VF. The tickle warning signal is a distinctive signal applied with a voltage sufficiently high so that the patient perceives the signal, yet not so high as to be painful. As noted, the signal may be applied using electrode 31 mounted near the device can. A voltage in the range of 5 to 10 volts is typically sufficient. The actual voltage for use with a particular patient may be set by the physician following implant of the device using the external programmer 102 (FIG. 2). To this end, the tickle warning signal is generated using a range of voltage values and the minimum voltage sufficient to ensure that the patient perceives the tickle voltage signal may then be selected. Depending upon the programming of the device, the tickle warning signal applied to the patient may be a continuous signal or instead may be modulated signal, such as a sequence of distinctive pulses. In general, any form of warning signal may be employed so long as the patient will recognize the warning.

An electronic warning signal is also transmitted from the implanted device, at step 208, using short range telemetry warning system 105 (FIG. 2). In use, once the patient feels the internal tickle signal, he or she manually places the handheld verification device 105 (also FIG. 2) near his or her chest. The telemetry transceiver, which is normally in sleep mode, is turned on by a magnet within the handheld device. The handheld device receives the transmitted signal and provides a confirmation of the warning. In this manner, verification is provided to the patient that the tickle sensation felt internally is indeed a warning of cardiac ischemia and the patient can take immediate and appropriate action. If the patient mistakenly believes that a tickle warning signal has been felt, even though the implanted device has not generated such a warning signal, the handheld verification device will not receive the alarm confirming signal and thus the handheld device will show no warning signal. In this manner, the patient is thereby assured that no warning has been issued.

The warning provided by the handheld device may be visual, audible, or both. A visual warning may be in the form of a text display or a blinking light. The handheld device is preferably a small lightweight device so that the patient will be able to easily carry the handheld device, perhaps clipped to a belt or other article of clothing. Depending upon the specific implementation, the handheld device may be configured with a button for the patient to push to initiate confirmation. If a warning signal has been transmitted from the implanted device, the handheld then displays the appropriate warning signal. If no warning signal has been transmitted, the handheld device instead displays a different "all clear" signal. In other implementations, the handheld device may be configured to relay the warning signal, perhaps via wireless communication, to the physician of the patient or to appropriate emergency personal.

Although not shown in FIG. 4, the handheld device may in turn transmit a verification signal back to the implanted device indicating that the patient has received and acknowledged the warning. If so, steps 206 and 208 are repeated until the verification signal is received. During that time, the implanted device continues to apply the internal tickle voltage and continues to transmit the short range warning signal. Once verification is received, the internal tickle voltage and the short range warning signal are then discontinued and processing returns to step 200. Preferably, each time steps 206-208 are repeated, the internal warning unit incrementally increases the tickle voltage. Hence, if the internal tickle voltage warning is not initially felt by the patient, perhaps because the patient is asleep, the voltage is continuously increased until the patient notices the internal warning. Preferably, the voltage incrementally increases up to some predetermined maximum tickle voltage.

Transmission of a verification signal from the handheld device to the implanted device requires that the handheld device have a transmitter built therein. In other implementations, the handheld device is not provided with a transmitter and so no verification signal is transmitted back to the implanted device. If so, the implanted device is preferably configured to apply the internal tickle warning and to transmit the short range verification signal for either a predetermined period of time or until the implanted device has determined that the episode of cardiac ischemia has terminated. As can be appreciated, a wide range of specific warning techniques and protocols may be employed in accordance with the invention and no attempt is made herein to recite all possible techniques.

Figure 5:
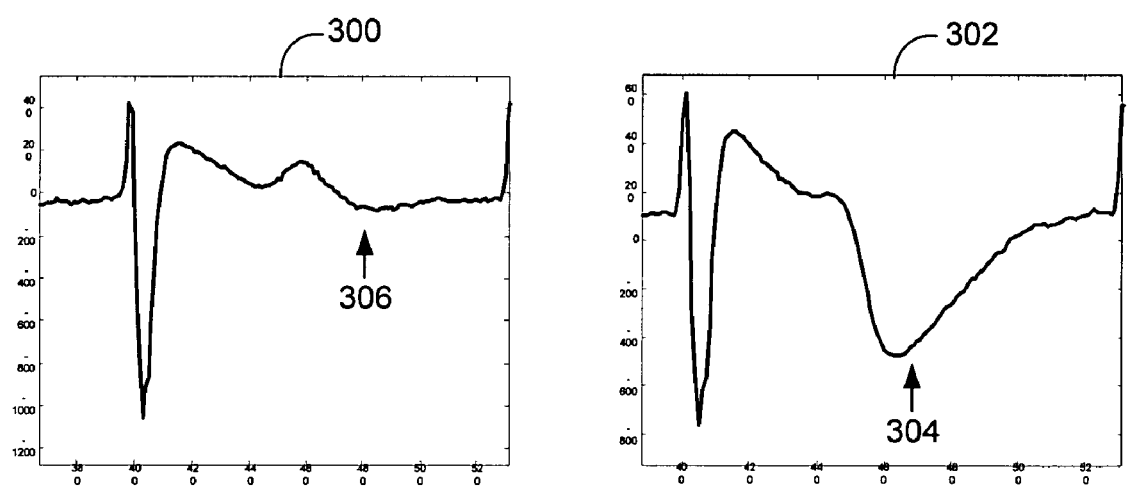
FIG. 5 is a graph illustrating simulated post-T-wave IEGM signal segments processed by the method of FIG. 4.

Thus, method of FIG. 4 operates to detect cardiac ischemia and to warn the patient. The technique exploits the recognition that post-T-wave segment of the IEGM is depressed following the T-wave during cardiac ischemia. This is shown in FIG. 5, which illustrates an IEGM signal 300 during a period of no cardiac ischemia and another IEGM signal 302 during an episode of cardiac ischemia. As can be seen, the segment of the IEGM subsequent to the T-wave is significantly depressed during the episode (segment 304) but is fairly uniform without otherwise (segment 306). This depression occurs immediately upon the occurrence of episodes of cardiac ischemia and so such episodes may be detected by first identifying the post-T-wave segments and then detecting the depression of the IEGM within the post-T-wave segments.

Figure 6:
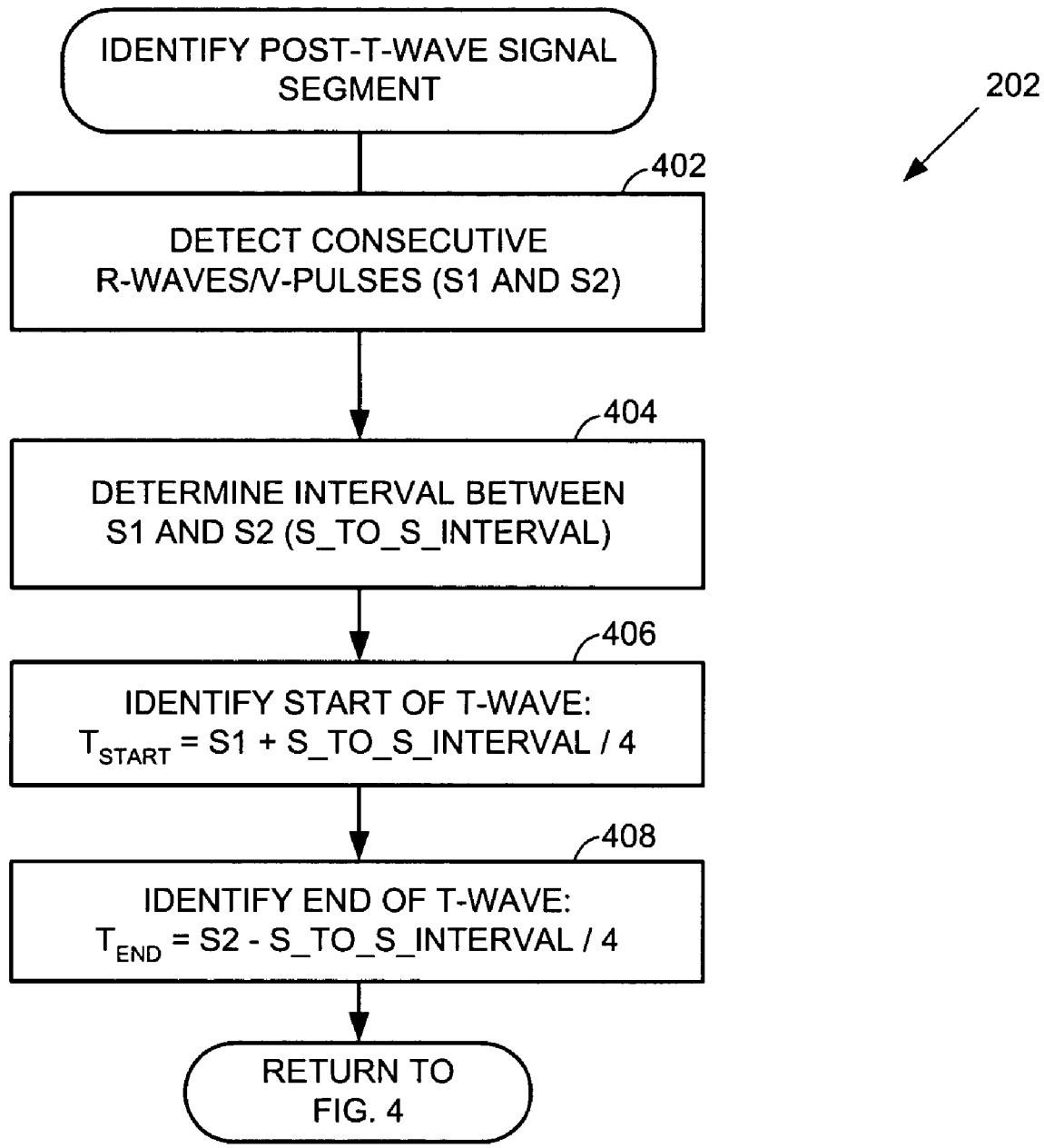
FIG. 6 is a flow chart illustrating an exemplary method for identifying a post-T-wave segment for use with the method of FIG. 4.

Referring now to FIG. 6 an exemplary technique will be described for identifying the post-T-wave signal segment for use at step 202 of FIG. 4. T-waves are often difficult to detect within ventricular IEGM signals and so the technique of FIG. 6 does not attempt to detect T-waves. Rather, R-waves/V-pulses are detected and the post-T-wave segment is identified relative to the R-wave/V-pulse. More specifically, at step 402, the latest pair of consecutive R-waves/V-pulses is detected with their respective event times designated as S1 and S2. The interval between S1 and S2 (referred to herein as the S_to_S_Interval) is calculated at step 404. The start of the post-T-wave segment ($T_{start}$) is then calculated at step 406 using:

$$T_{start}=S1+S\_to\_S\_Interval/M.$$

The end of the post-T-wave segment ($T_{end}$) is then calculated at step 408 using:

$$T_{end}=S2-S\_to\_S\_Interval/N.$$

M and N are integers. With these formulae, if the ventricular rate is 60 beats per minute (bpm) and M=N=4, then the S_to_S_Interval is one second in duration and $T_{start}$ is thereby set to a point in time 0.25 seconds after S1 and $T_{end}$ is set to a point in time 0.25 seconds before S2 (or 0.75 seconds after S1). The post-T-wave segment thereby has a duration of 0.5 seconds. If the ventricular rate is instead 120 bpm, then the S_to_S_Interval is 0.5 seconds and $T_{start}$ is set to a point in time 0.125 seconds after S1 and $T_{end}$ is set to a point in time 0.125 seconds before S2 (or 0.875 seconds after S1). The post-T-wave segment thereby has a duration of 0.75 seconds. Hence, the duration of the post-T-wave segments and their relative starting and ending points vary according to ventricular rate.

Thus, the start and end points of the post-T-wave segment are derived from the latest pair of R-wave/V-pulses. In other embodiments, actual T-waves can be detected within the ventricular IEGM signals and the post-T-wave segment calculated based on the T-wave. As noted, identifying the post-T-wave segment based only on R-wave/V-pulses is preferred since T-waves are often hard to detect. In any case, once the start and end points of the latest post-T-wave segment are identified, processing returns to FIG. 4.

Figure 7:
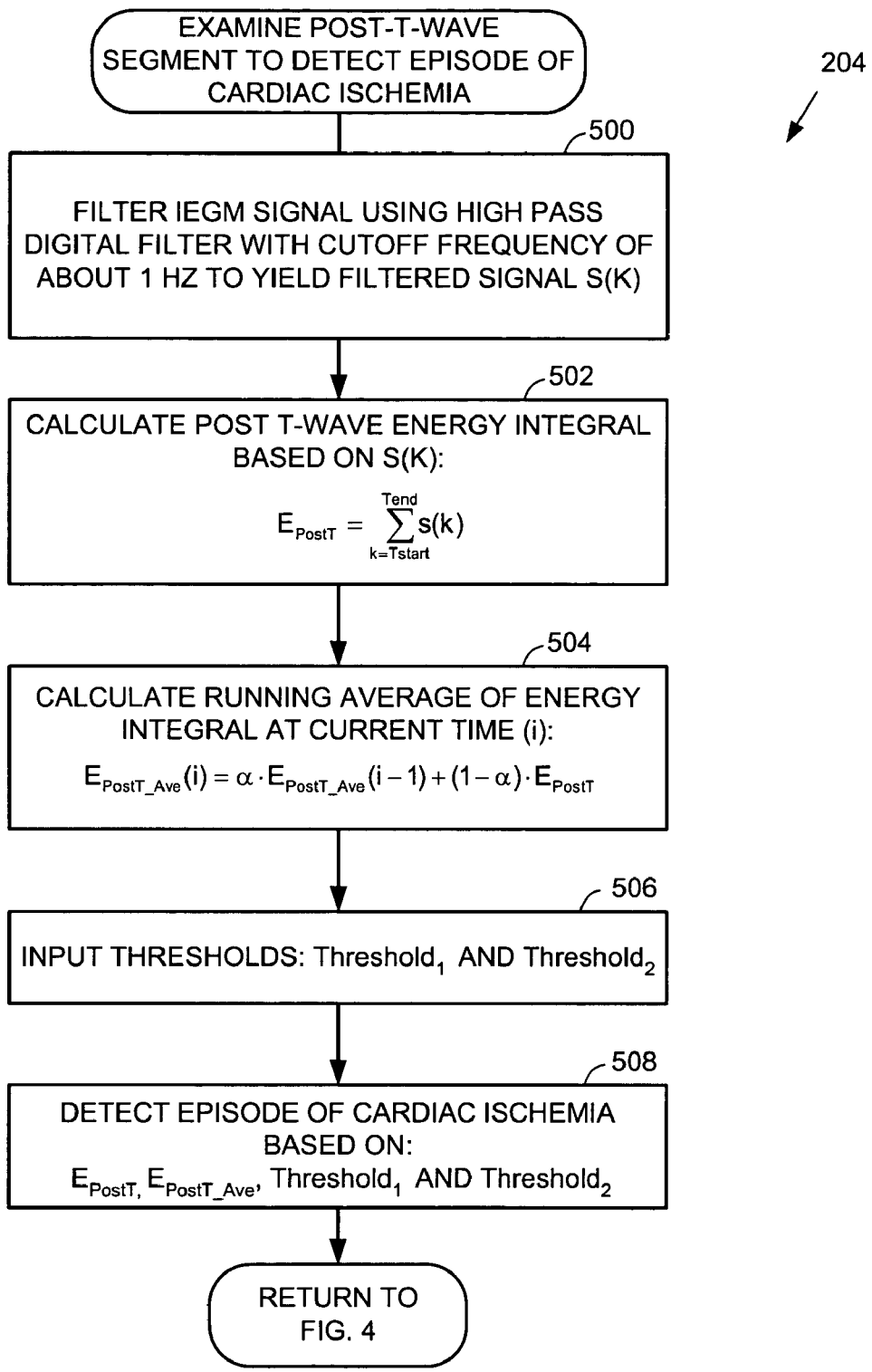
FIG. 7 is a flow chart illustrating an exemplary method for examining the post-T-wave segment for use with the method of FIG. 4 to detect cardiac ischemia.

Referring to FIG. 7, a specific exemplary technique will be described for identifying the cardiac ischemia for use at step 204 of FIG. 4. The technique employs an energy integral signal representative of the degree to which the IEGM drops during the post-T-wave segment along with a running average of the energy integral, which are compared against first and second thresholds indicative of the onset of an episode of cardiac ischemia. Initially, at step 500, the ventricular IEGM signals are filtered using the digital highpass filter. Note that any constant or DC signal, such as a signal having a uniform voltage of 50 millivolts (mV), is completely filtered out by the highpass filter. The post-T-wave signal segment tends to shift its energy towards lower frequencies (lower than the highpass filter cutoff frequency) during an episode of cardiac ischemia. Thus, when cardiac ischemia is present, the highpass filter creates a drop at the post-T signal segment, thus creating a post-T-wave notch. On the other hand, when ischemia is not present, the post-T-wave segment passes through the high pass filter without attenuation and no post-T-wave notch occurs. An integral of the filtered version of the IEGM signal thereby provides a measure of the extent to which the unfiltered version of the IEGM signal is non-uniform and therefore provides a measure of the extent to which the signal varies with time.

Figure 8:
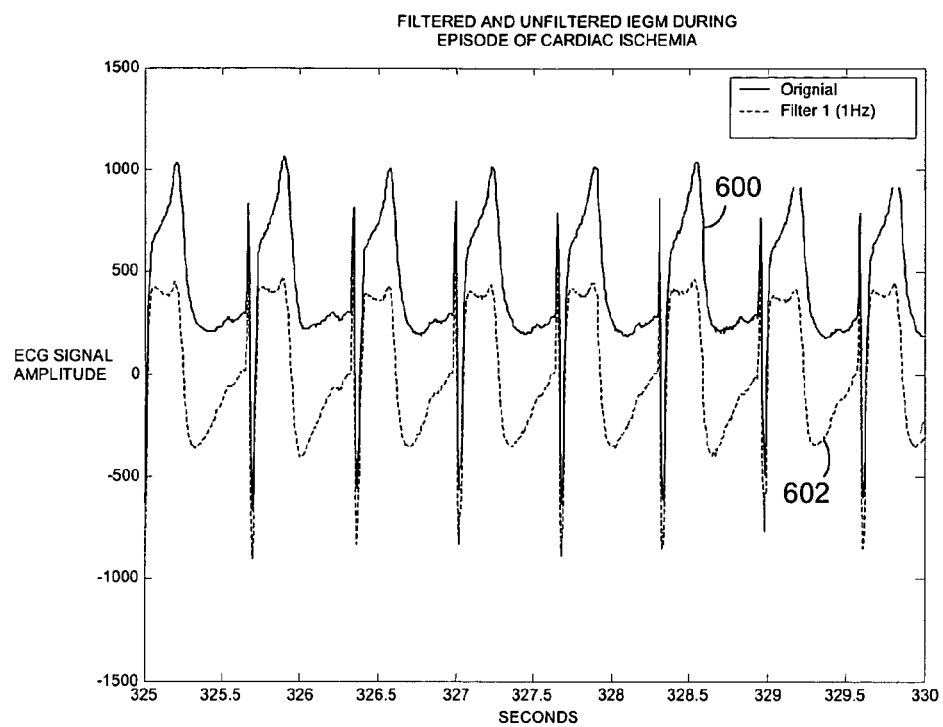
FIG. 8 is a graph illustrating a simulated IEGM signal during an episode of cardiac ischemia along with a version of the simulated IEGM signal filtered in accordance with the method of FIG. 7.
Figure 9:
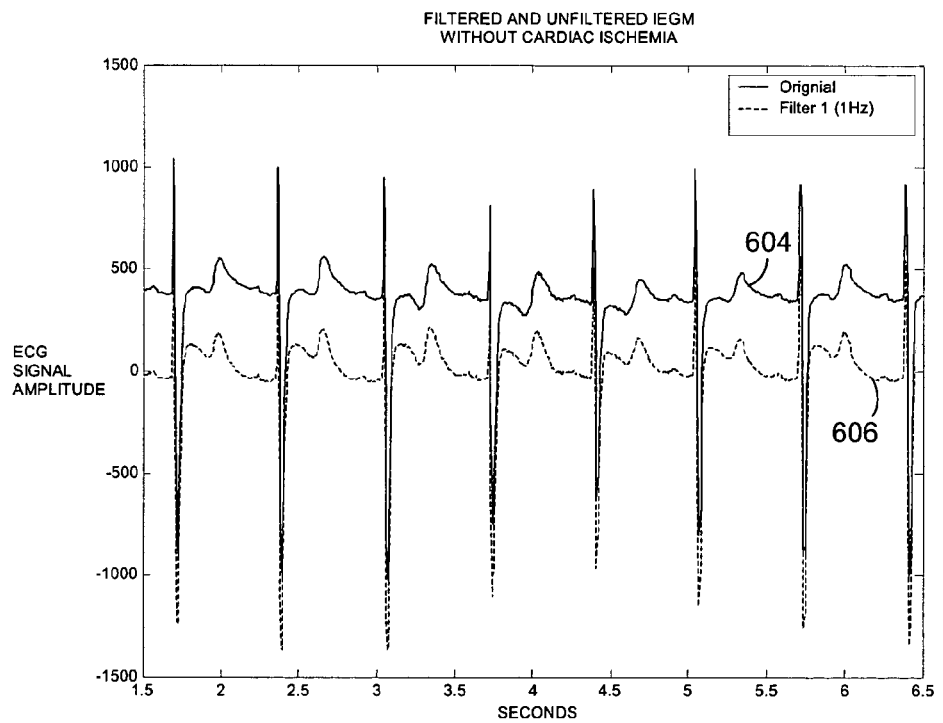
FIG. 9 is a graph illustrating a simulated IEGM signal during a normal sinus rhythm along with a version of the simulated IEGM signal filtered in accordance with the method of FIG. 7.

Highpass filtering of IEGM signals is shown in FIGS. 8 and 9 for an episode of cardiac ischemia and for a non-ischemia, respectively. More specifically, FIG. 8 illustrates an unfiltered IEGM signal 600 recorded during the episode of cardiac ischemia along with a filtered version 602 of the same IEGM signal filtered using a highpass filter with a cutoff frequency of 1 Hz. The unfiltered IEGM signal shows a significant drop-off following the T-wave and so the filtered IEGM signal deviates significantly from the baseline voltage or amplitude of zero during the post-T-wave segment. In contrast, FIG. 9 illustrates an unfiltered IEGM signal 604 for a normal sinus rhythm along with a filtered version 606 of the IEGM, again subject to a highpass filter with a cutoff frequency of 1 Hz. The unfiltered IEGM signal shows no significant drop-off following the T-wave and is instead fairly uniform. Thus, the filtered signal does not deviate significantly from the baseline voltage of zero during the post-T-wave segment while there is no ischemia but deviates significantly during the episode of cardiac ischemia. Hence, an integral of the energy of the filtered IEGM signal during the post-T-wave segment is relatively small while there is no cardiac ischemia but is significantly negative during cardiac ischemia. By comparing the energy integral and its running average against appropriate thresholds, cardiac ischemia is thereby detectable. Note that, within FIGS. 8 and 9 and within all other IEGM graphs provided herein, the IEGM signals are simulated signals provided to illustrate features of the invention and should not be construed as being necessarily representative of clinical IEGM data. The simulated IEGM signals were derived from surface electrocardiogram (ECG) signals filtered to yield the simulated IEGM signals.

Returning now to FIG. 7, the total energy within the filtered IEGM signals contained within the post-T-wave segment is summed or integrated at step 502 by calculating:

$$E_{PostT} = \sum_{k=Tstart}^{Tend} s(k)$$

where s(k) are individual digital samples of the filtered ventricular IEGM, i.e. each individual value of s(k) represents a single amplitude value, which may be positive or negative. Since s(k) can take on negative values, $E_{PostT}$ can also take on negative values. With a sampling frequency of 200 Hz, a post-T-wave segment of 0.5 seconds in duration contains 100 data points to be processed, i.e. there are 100 values of k to be summed within the segment.

At step 504, the running average of the energy integral is calculated at a point in time "i" using:

$$E_{PostT\_Ave}(i) = \alpha \cdot E_{PostT\_Ave}(i-1) + (1-\alpha) \cdot E_{PostT}$$

where $\alpha$ is a predetermined "forgetting" value, which ensures that the running average is heavily weighted based on recent values of $E_{PostT}$. The value $\alpha$ is typically set in the range of 0.9 and 0.95 and is preferably set to 15/16. The value of 15/16 is preferred because it allows for elimination of a multiplication operation in the calculation of $E_{PostT\_Ave}$ by instead permitting a shift operation. The initial running average value $E_{PostT\_Ave}(0)$ is preset to a default value, preferably zero. First and second thresholds (Threshold$_1$ and Threshold$_2$) are retrieved from memory, at step 506, and then $E_{PostT}$, $E_{PostT\_Ave}$, Threshold$_1$ and Threshold$_2$ are collectively used to detect cardiac ischemia at step 508 using a state machine shown in FIG. 10 and described below.

In the exemplary embodiment using a cutoff frequency of 1 Hz and the sampling frequency of 200 Hz and using floating point arithmetic, Threshold, is typically set in the range of 1200 to 2800 and is preferably set to 2200. Threshold$_2$ is typically set in the range of 1000 to 3000 and is preferably set to 2800. Both values assume that absolute values are taken of $E_{PostT\_Ave}$ and of $E_{PostT\_Ave} - E_{PostT} - E_{PostT\_Ave}$. More specifically, $|E_{PostT} - E_{PostT\_Ave}|$ is compared against Threshold$_1$ and $|E_{PostT\_Ave}|$ is compared against Threshold$_2$. $|E_{PostT} - E_{PostT\_Ave}|$ provides a measure of the extent to which individual values of $E_{PostT}$ are dropping faster than its running average. As noted, when an episode of cardiac ischemia occurs, $E_{PostT}$ quickly becomes strongly negative, but it takes a much longer time for its running average to catch up to $E_{PostT}$. Hence, the amount of lag between $E_{PostT\_Ave}$ and $E_{PostT}$ can be used to detect the episode of cardiac ischemia.

Note that the choice of Threshold$_1$ and Threshold$_2$ may vary depending upon the sampling frequency, which affects the total number of data samples summed within each post-T-wave segment. The choice of thresholds may also depend upon the cutoff frequency. The ventricular rate of the patient also affects the total number of data samples summed within each post-T-wave segment, since the ventricular rate affects the length of the post-T-wave segment. Hence, for a given sampling rate and cutoff frequency, Threshold$_1$ and Threshold$_2$ are preferably set values sufficient to ensure that changes in ventricular rate do not affect the detection of cardiac ischemia. Routine experimentation may be used to identify suitable values for Threshold$_1$ and Threshold$_2$ for a given sampling rate, cutoff frequency and for a range of expected ventricular rates.

Figure 10:
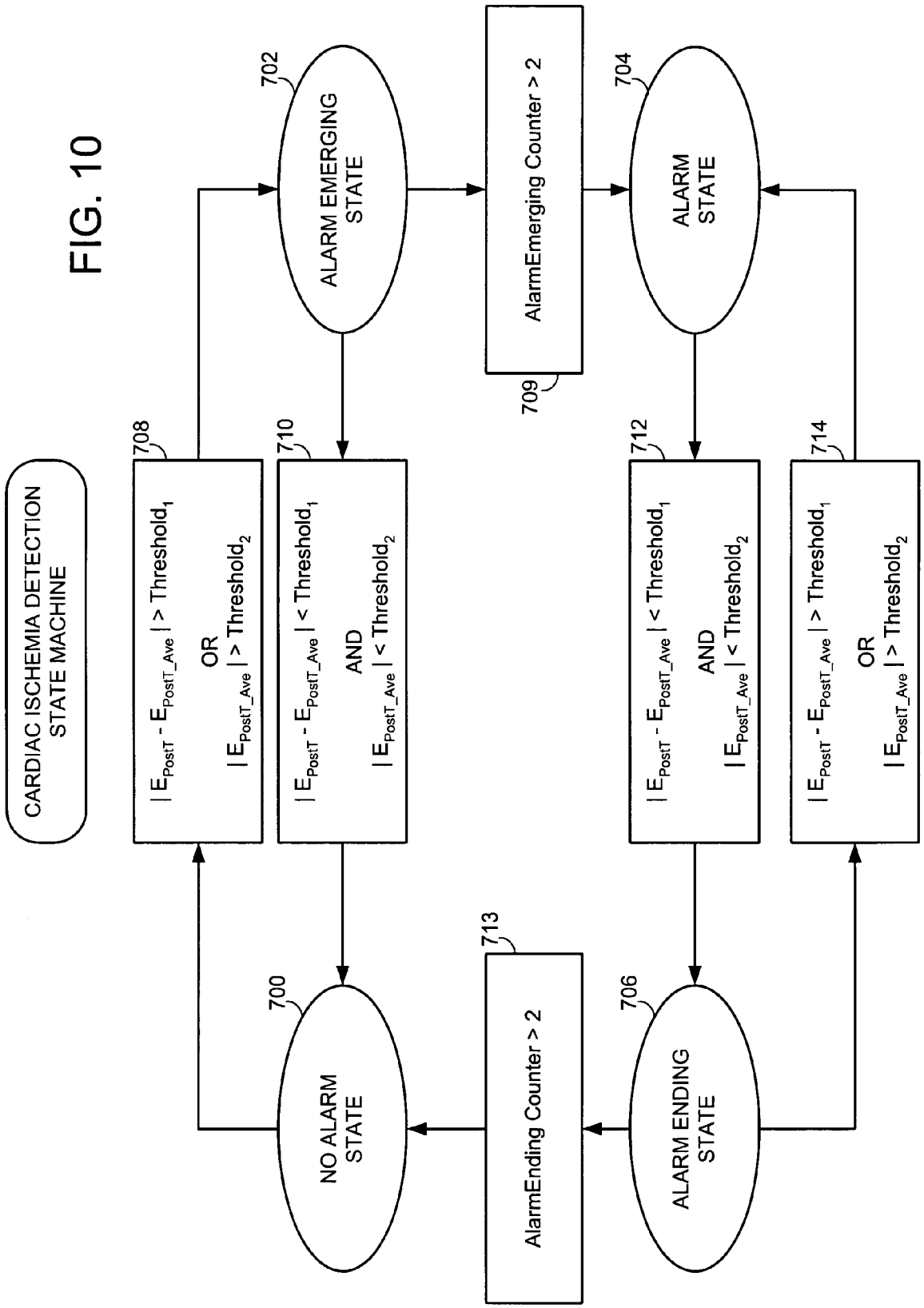
FIG. 10 is a flow chart illustrating an exemplary state machine for use with the method of FIG. 7 for detecting the onset and termination of an episode of cardiac ischemia.

Referring now to FIG. 10, a state machine diagram illustrates an exemplary technique for detecting cardiac ischemia using the latest values for $E_{PostT}$ and $E_{PostT\_Ave}$ calculated by the technique of FIG. 7. Briefly, the cardiac ischemia alarm or warning is triggered if either threshold is exceeded for three consecutive heart beats. The alarm is not deactivated until both the thresholds are no longer met for three consecutive heart beats. More specifically, the state machine has four states: a "No Alarm" 700, an "Alarm Emerging" 702, an "Alarm" 704, and an "Alarm Ending" 706. The state machine begins in the No Alarm state then, if either of thresholds is exceeded, as indicated by logic block 708, the state machine transitions to the Alarm Emerging state and an Alarm Emerging counter is incremented. (The counter is initially set to zero.) For each consecutive heart beat (or cycle) for which either threshold is exceeded, the AlarmEmerging counter is incremented. Once the AlarmEmerging counter is greater than two, as indicated by logic block 709, the state machine transitions to Alarm state 704 and the above-described tickle warning and short-range telemetry warning signals are issued. However, if while in the Alarm Emerging state, neither of the thresholds are met for any one cycle, as indicated by logic block 710, then the AlarmEmerging counter is reset to zero and the state machine returns to the No Alarm state and the AlarmEmerging counter is reset to zero. In other words, if $|E_{PostT} - E_{PostT\_Ave}|$ falls below Threshold$_1$ and $|E_{PostT\_Ave}|$ falls below Threshold$_2$, then the state machine returns to the No Alarm state.

The main reason for the Alarm Emerging state is to address the case where $E_{PostT}$ has a spike. It takes some multiple number of cycles before $E_{PostT\_Ave}$ catches up to $E_{PostT}$. (This depends upon the selection of the forgetting factor $\alpha$. For example, if $\alpha$ is set to 15/16, then it takes about 16 cycles before $E_{PostT\_Ave}$ catches up to $E_{PostT}$.) When a true episode of cardiac ischemia occurs, $E_{PostT}$ increases from one cycle to the next and so $E_{PostT}$ remains larger than the $E_{PostT\_Ave}|$ Ave for at least 16 cycles (assuming the forgetting factor $\alpha$ is set to 15/16). By requiring that the AlarmEmerging counter reach three before transitioning to the Alarm state, temporary spikes in $E_{PostT}$ will not trigger the alarm. In any case, once the state machine is in the Alarm state, it remains there until both of the thresholds are no longer exceeded, as indicated by logic block 712, then the state machine transitions to the Alarm Ending state and AlarmEnding counter is incremented. (The counter is also initially set to zero.) For each consecutive heart beat for which both of the thresholds are not met, the state machine remains in the Alarm Ending state and the AlarmEnding counter is incremented. Once the AlarmEnding counter is greater than two, as indicated by logic block 713, the state machine returns to the No Alarm state and another warning cannot be issued again until passing through the Alarm Emerging state. However, if for any heart beat while in the Alarm Ending state, either of the thresholds are again exceeded, as indicated by logic block 714, then the state machine returns to the Alarm state.

Note that, with the state machine, the cardiac ischemia flag is set at all times while in either the Alarm or Alarm Ending states. The flag is not set while in either the No Alarm or the Alarm Emerging state. Cardiac ischemia warnings may be issued only while the flag is set. However, the warnings need not be continuously issued at all times while the flag is set. Rather, as explained above, the tickle warning may be pulsed. Both the tickle warning and short range telemetry warning may be discontinued once the patient has acknowledged the warning. Hence, additional logic may be used to further control the generation of the warning signals, beyond what is shown in FIG. 10.

Figure 11:
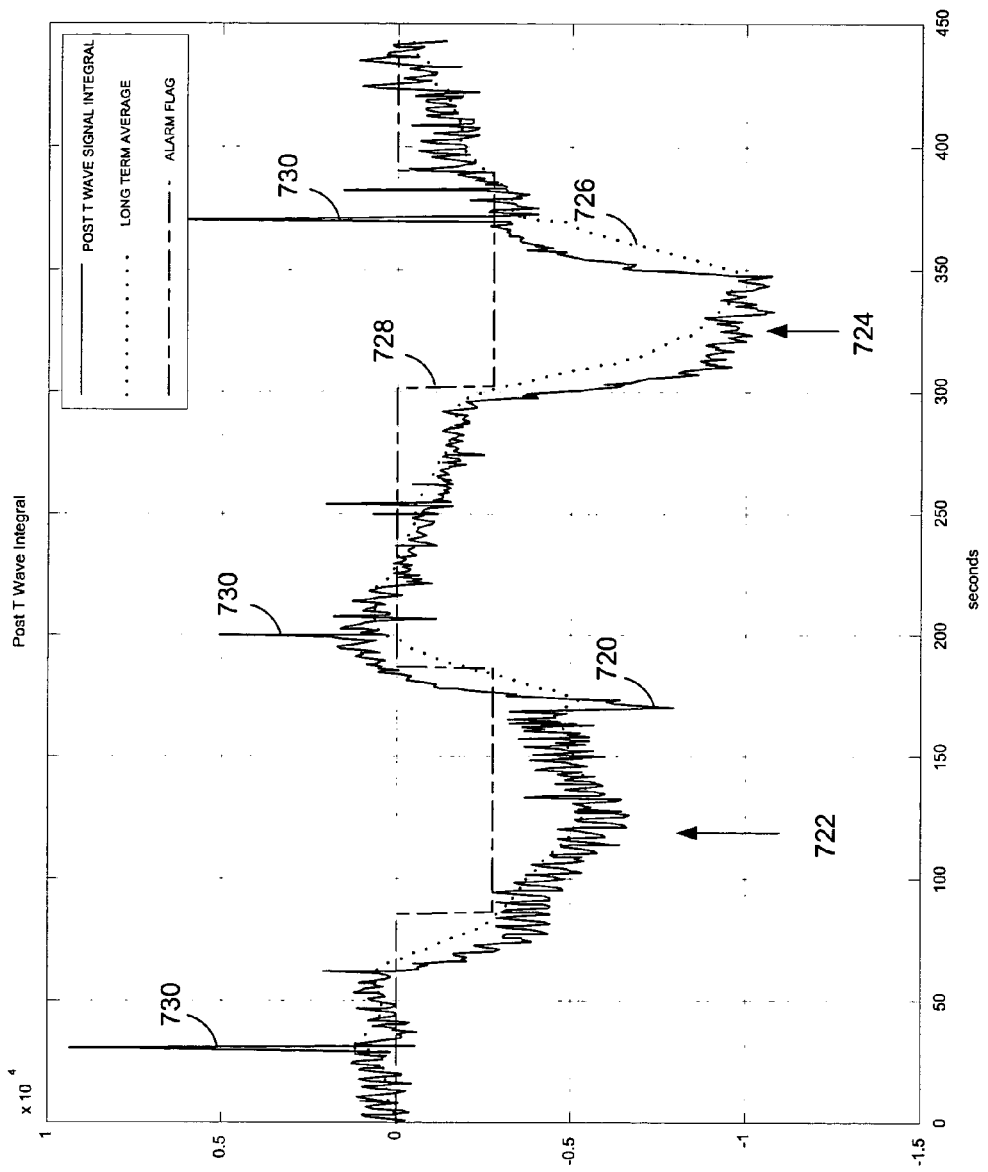
FIG. 11 is a graph illustrating simulated post-T-wave signal integrals calculated using the method of FIG. 7 during two episodes of cardiac ischemia along with a running average of the signal integrals and a cardiac ischemia flag indicative of cardiac ischemia.

An exemplary signal integral $E_{PostT}$ and running average $E_{PostT\_Ave}$ are illustrated in FIG. 11 along with an alarm flag signal. More specifically, FIG. 11 illustrates exemplary $E_{PostT}$ values 720, which vary during a period of about 450 seconds that includes two episodes of cardiac ischemia 722 and 724. The first episode 722 commences at about the 50 second mark and terminates at about the 170 second mark. The second episode 724 commences at about the 290 second mark and terminates at about 340 second mark. As can be seen, the energy integral drops significantly during each episode of cardiac ischemia. FIG. 11 also illustrates exemplary $E_{PostT\_Ave}$ values 726. As can be seen, $E_{PostT\_Ave}$ generally lags $E_{PostT}$. With this data, the Alarm flag 728 is set at about the 80 second mark (i.e. it is at this point that the state machine enters the Alarm state). A first cardiac ischemia warning is thus issued fairly promptly after the corresponding episode of cardiac ischemia commences. The Alarm flag is deactivated at about the 180 second mark (i.e. it is at this point that the state machine returns to the No Alarm state). The Alarm flag is set again at about the 305 second mark, which is shortly after the second episode of ischemia commences. The Alarm flag is deactivated at about the 380 second mark. Note that within the FIG. 11, three spikes 730 are shown in the $E_{PostT}$ values. As can be seen, the state machine logic properly ignores the spikes. The data shown in FIG. 11 was derived from data detected from a human test subject using a surface ECG, filtered to simulate IEGM signals, then processed using the technique described above. The episodes of ischemia were a triggered by inflation of a balloon within a selected artery leading into heart muscle. The spikes in the data appear to have occurred as a result of movement of the surface EKG leads. Any spikes occurring with actual IEGM data are not likely to be as significant. In any case, the data within FIG. 11 should be regarded as a simulation data provided for the purposes of illustrating the invention and should not be regarded as actual clinical data. In any case, as shown within the FIG. 11, warning signals are generated fairly promptly after the commencement of each episode of cardiac ischemia. As noted, these episodes typically occur at least half an hour and sometimes more than 24 hours prior to an AMI. Accordingly, ample warning is provided to the patient, allowing the patient time to consult a physician or proceed to an emergency room.

Figure 12:
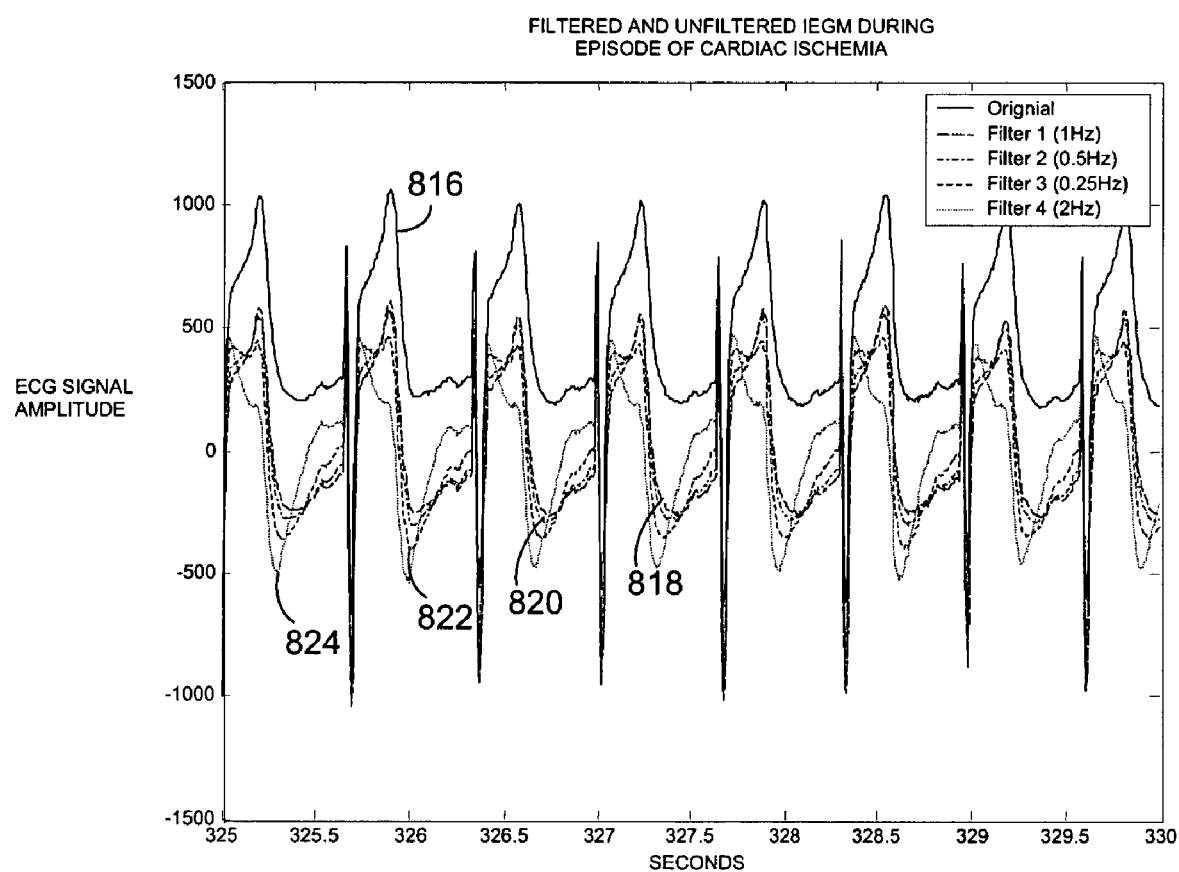
FIG. 12 is a graph illustrating the simulated IEGM signal of FIG. 9 along with various filtered versions generated using highpass filters with different cutoff frequencies.

In the forgoing examples, a highpass filter cutoff frequency of 1 Hz is used. Other appropriate cutoff frequencies may be used as well. The effect of various filter cutoff frequencies is illustrated in FIG. 12. An unfiltered IEGM 816 is shown, along with filtered versions filtered subject to cutoff frequencies of 1 Hz (line 818), 0.5 Hz (line 820), 0.25 Hz (line 822), and 2 Hz (line 824). As can be seen, each of the filtered versions provides a significant enhancement of the post-T-wave notch and so each yields a significant post-T-wave signal integral value. In the example, the cutoff frequency of 2 Hz provides the sharpest post-T-wave downward notch. However, with appropriately chosen thresholds, any of the filtered versions can yield signal integral values sufficient to trigger cardiac ischemia warnings.

Note that, unlike certain previous cardiac ischemia detection techniques, which require a low filter cutoff frequency such as, for example, 0.1 Hz, the technique of the invention can employ higher cutoff frequencies, and hence does not require a large capacitor. The optimal cut-off frequency may depend upon the particular lead configuration used to detect the ventricular IEGM signals and on the configuration of circuit components of the implanted device used to receive and process the ventricular IEGM, such as ventricular sense amplifiers and the like. Hence, no attempt is made herein to specify an optimal cutoff frequency nor to specify the upper and lower bounds of acceptable cutoff frequencies. Routine experimentation may be performed to identify a range of acceptable cut-off frequencies for use with particular implanted devices. In general, though, cutoff frequencies in the range of 0.1 Hz-5 Hz are usually suitable.

In general, a wide variety of techniques can be implemented consistent with the principles the invention and no attempt is made herein to describe all possible techniques. Although described primarily with reference to an example wherein the implanted device is a defibrillation/pacer, principles of the invention are applicable to other implantable medical devices as well. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable medical device for implant within a patient, a method comprising:

receiving electrical cardiac signals having a series of cycles, each cycle including a ventricular repolarization followed by a ventricular depolarization;

identifying segments of the cardiac signals subsequent to a ventricular repolarization and prior to the ventricular depolarization following the ventricular repolarization;

taking a difference between the total amount of energy in one of the identified segments and the running average of the total amount of energy in a plurality of the identified segments and comparing said difference to a first threshold;

comparing just the running average to a second threshold; and detecting cardiac ischemia if either the first threshold or the second threshold is exceeded for a predetermined number of heart beats.

2. The method of claim 1 further comprising routing the cardiac signals through a high-pass filter operative to pass all signals above a cutoff frequency, to yield a high-pass filtered signal.

3. The method of claim 2 wherein the cutoff frequency is in the range of 0.1 to 5.0 Hz.

4. The method of claim 2 wherein the cutoff frequency is at least 1 Hz.

5. The method of claim 1 wherein the total amount of energy in an identified segments is derived by calculating:

$$E_{PostT} = \sum_{k=Tstart}^{Tend} s(k)$$

wherein s(k) is a digitized version of the filtered cardiac signal, $T_{start}$ and $T_{end}$ are start and end points, respectively, of the identified segment, and k represents individual samples of the digitized signal.

6. The method of claim 5 further comprising initially calculating $T_{start}$ and $T_{end}$ by:
   identifying a pair of consecutive ventricular depolarizations (S1 and S2) within the cardiac signals;
   determining a time interval (S_to_S_Interval) between S1 and S2;
   setting $T_{start}$ equal to S1+S_to_S_Interval/4; and
   setting $T_{end}$ equal to S2−S_to_S_Interval/4.

7. The method of claim 1 wherein the running average of a plurality of identified segments is derived by calculating:

$$E_{PostT\_Ave}(i) = \alpha \cdot E_{PostT\_Ave}(i-1) + (1-\alpha) \cdot E_{Post}$$

at time increment "i" where α is a predetermined value and wherein $E_{PostT\_Ave}(0)$ is set to a default value.

8. The method of claim 7 wherein α is equal to 15/16.

9. The method of claim 1 wherein, during comparing, the absolute value of the difference between the total amount of energy in one of the identified segments and the running average of the total amount of energy in a plurality of the identified segments is compared to the first threshold, and the absolute value of the running average is compared to the second threshold.

10. The method of claim 1 further comprising detecting the end of an episode of ischemia if both the first threshold and the second threshold are not exceeded for a predetermined number of heart beats.

11. The method of claim 1 further comprising:
   generating a warning signal if ischemia is detected.

12. The method of claim 11 wherein generating a warning signal comprises:
   applying a perceptible electrical notification signal to subcutaneous tissue.

13. The method of claim 11 wherein generating a warning signal comprises:
   transmitting a notification signal to a warning device external to the patient.

14. An implantable medical device comprising:
   a sensing system operative to receive electrical cardiac signals having a series of cycles, each cycle including a ventricular repolarization followed by a ventricular depolarization, and to identify segments of the cardiac signals subsequent to a ventricular repolarization and prior to the ventricular depolarization following the ventricular repolarization;
   a signal integration unit operative to determine energy values representative of a total amount of energy within identified segments; and
   a threshold comparison unit operative to:
      take a difference between the total amount of energy in one of the identified segments and the running average of the total amount of energy in a plurality of the identified segments and compare said difference to a first threshold;
      compare just the running average to a second threshold; and
      detect cardiac ischemia if either the first threshold or the second threshold is exceeded for a predetermined number of heart beats.

15. In an implantable medical device for implant within a patient, a system comprising:
   means for receiving electrical cardiac signals having a series of cycles, each cycle including a ventricular repolarization followed by a ventricular depolarization;
   means for identifying segments of the cardiac signals subsequent to a ventricular repolarization and prior to the ventricular depolarization following the ventricular repolarization;
   means for deriving energy values representative of a total amount of energy within identified segments;
   means for taking a difference between the total amount of energy in one of the identified segments and the running average of the total amount of energy in a plurality of the identified segments and comparing said difference to a first threshold;
   means for comparing just the running average to a second threshold; and
   means for detecting cardiac ischemia if either the first threshold or the second threshold is exceeded for a predetermined number of heart beats.

* * * * *